(12) United States Patent
Meng et al.

(10) Patent No.: US 11,131,040 B2
(45) Date of Patent: Sep. 28, 2021

(54) ANTIMICROBIAL ALGINATE FIBER, AND PREPARATION METHOD FOR AND USE OF DRESSING THEREOF

(71) Applicant: Huizhou Foryou Medical Devices Co., Ltd., Huizhou (CN)

(72) Inventors: Yonggang Meng, Huizhou (CN); Jinwen Mo, Huizhou (CN)

(73) Assignee: HUIZHOU FORYOU MEDICAL DEVICES CO., LTD., Huizhou (CN)

( * ) Notice: Subject to any disclaimer, the term of this patent is extended or adjusted under 35 U.S.C. 154(b) by 78 days.

(21) Appl. No.: 16/428,854

(22) Filed: May 31, 2019

(65) Prior Publication Data

US 2019/0284727 A1 Sep. 19, 2019

Related U.S. Application Data

(63) Continuation-in-part of application No. PCT/CN2017/094221, filed on Jul. 25, 2017.

(51) Int. Cl.
| | | |
|---|---|---|
| *D01F 9/04* | (2006.01) | |
| *A61F 13/00* | (2006.01) | |
| *A61L 15/28* | (2006.01) | |
| *D01F 11/00* | (2006.01) | |
| *D06M 15/564* | (2006.01) | |
| *A61L 15/46* | (2006.01) | |
| *A61L 15/42* | (2006.01) | |

(52) U.S. Cl.
CPC .......... *D01F 9/04* (2013.01); *A61F 13/00063* (2013.01); *A61L 15/28* (2013.01); *A61L 15/46* (2013.01); *D01F 11/00* (2013.01); *D06M 15/564* (2013.01); *A61F 2013/00229* (2013.01); *A61L 15/42* (2013.01); *A61L 2300/206* (2013.01); *A61L 2300/404* (2013.01)

(58) Field of Classification Search
None
See application file for complete search history.

(56) References Cited

U.S. PATENT DOCUMENTS

| | | |
|---|---|---|
| 949,964 A | 2/1910 | Schmidt et al. |
| 5,744,151 A | 4/1998 | Capelli |
| 6,093,414 A | 7/2000 | Capelli |
| 6,696,077 B2 | 2/2004 | Scherr |
| 6,719,987 B2 | 4/2004 | Burell et al. |
| 7,229,689 B2 | 6/2007 | Qin et al. |
| 7,714,783 B2 | 5/2010 | Caskey |
| 8,921,427 B2 | 12/2014 | Rohrer et al. |
| 9,000,252 B2 | 4/2015 | Bradford et al. |
| 9,345,805 B2 | 5/2016 | Woods |
| 9,499,641 B2 | 11/2016 | Li |
| 2009/0306157 A1 | 12/2009 | Rohrer et al. |
| 2010/0215723 A1 | 8/2010 | Yao |
| 2015/0335492 A1 | 11/2015 | Tao et al. |

FOREIGN PATENT DOCUMENTS

| | | |
|---|---|---|
| CN | 1935268 A | 3/2007 |
| CN | 101381907 A | 11/2009 |
| CN | 102462860 A | 5/2012 |
| CN | 103835025 B | 12/2015 |
| CN | 103768643 B | 4/2016 |
| CN | 105709262 A | 6/2016 |
| CN | 105963755 A | 9/2016 |
| CN | 105999362 A | 10/2016 |
| CN | 106049036 A | 10/2016 |
| CN | 106075534 A | 11/2016 |
| GB | 2504872 A | 2/2014 |

OTHER PUBLICATIONS

European search report, EP17919151, dated Jul. 9, 2020 (6 pages).

*Primary Examiner* — Jessica Worsham

(57) ABSTRACT

The present disclosure provides an antimicrobial alginate fiber, a method for manufacturing an antimicrobial alginate fiber dressing thereof, and an application thereof. When the cationic polymer polyhexamethylene guanide salt is mixed with the anionic polymer alginate, the antimicrobial activity of the guanide salt is quickly passivated. The present disclosure achieves a lower content of polyhexamethylene guanide salt in an alginate dressing with good long-term antimicrobial activities. The polyhexamethylene guanide salt has a low dissolution rate, and significantly reduces a potential risk of carcinogenicity, mutagenicity and reproductive toxicity.

8 Claims, 3 Drawing Sheets

ANTIMICROBIAL ALGINATE FIBER, AND PREPARATION METHOD FOR AND USE OF DRESSING THEREOF

CROSS-REFERENCE TO RELATED APPLICATIONS

The present application is a continuation-in-part of International (PCT) Patent Application No. PCT/CN2017/094221, filed on Jul. 25, 2017, the entire contents of which are hereby incorporated by reference.

TECHNICAL FIELD

The described embodiments relate to a medical field of wound care or wound healing; and more particularly, to a manufacturing method and application of an antimicrobial alginate fiber and dressing materials thereof.

BACKGROUND

The alginate dressing may form a soft gel, after absorbing fluid exudating from a wound, providing an ideal moist environment for promoting wound healing and relieving wound pain. The alginate dressing has advantages of safety, non-toxicity, high hygroscopicity, hemostasis, gelation, and promoting wound healing, so that it is widely used in the field of wound care. However, the alginate dressing is lack of antimicrobial properties.

Because polyhexamethylene biguanide salt is highly cationic, and absorbs various kinds of bacteria and viruses, which are usually negatively charged, entering cell membranes to inhibit synthesis of liposome in the cell membrane, causing apoptosis of the bacteria, so that the polyhexamethylene biguanide salt achieves bactericidal effects. The polyhexamethylene biguanide salt has broad spectrum sterilization and is very widely used in wound management. The polyhexamethylene biguanide salt has been proved to have a positive effect on wound healing and to reduce pain, unpleasant smells and formation of carrion. The polyhexamethylene biguanide salt is a good substitute for silver, honey, or iodine, and is widely used in antimicrobial wound dressings.

However, the polyhexamethylene biguanide salt has potential carcinogenicity, mutagenicity and reproductive toxicity at higher levels. A new act enacted by the European Commission for Consumer Safety Science (SCCS) in April 2017 set the safety limit for the polyhexamethylene biguanide salt to 0.1%. Further, the polyhexamethylene biguanide salt, which is a cationic polymer, and alginate, which is an anionic polymer, can have an ionic complexation reaction, which passivates the antimicrobial property. In order to achieve the antimicrobial effect, a high level of polyhexamethylene biguanide salt needs to be added.

Chinese patent CN106075534A publishes a chitosan alginate dressing which combines advantages of chitosan and traditional alginate dressing. The chitosan alginate dressing has antimicrobial, wound healing and other properties, and enhances the original advantages of the alginate dressing, such as hemostatic, hygroscopic, and moisturizing properties. However, the chitosan itself is not a broad spectrum antimicrobial agent, the antimicrobial activity can barely meet the expected requirement. Therefore, the product is weak at anti microbes.

A Chinese patent CN105999362A discloses a medical alginate compound dressing containing antimicrobial medicines. The medicine causes drug resistance and has other potential adverse side effects.

Chinese patents CN105536041A, and U.S. Pat. No. 7,714,183 disclose an antimicrobial alginate compound dressing containing honey. The antimicrobial alginate compound dressing has good anti-infectious effect, but a high level of honey is required, which increases manufacture cost.

Chinese patents CN105963755A, CN201610149152.7, and CN103768643B, and U.S. Pat. Nos. 7,714,183, 6,719,987, 9,345,805, 7,229,689, 6,696,077, 6,093,414, 5,744,151 disclose an alginate dressing containing silver ions which has good antimicrobial properties. A silver-containing alginate dressing is widely used in clinical practice, but when an organism absorbs silver, it causes toxicity and occurrence of drug-resistant microorganisms. An in vitro cellular study discovered that, the silver-containing alginate dressing affects cell morphology of keratinocytes and fibroblasts, reduces fibroblast regeneration, and inhibits collagen synthesis in fibroblasts, so that the silver-containing alginate dressing hinders wound healing and produces sustained cytotoxicity. Silver can enter body's cells to induce a potential risk of neurodegenerative diseases. Another study shows that, low doses of silver repeatedly acting on wounds can also produce microbial resistance. In vitro experiments also demonstrated similar results.

Chinese patents CN106049036A, CN101721734A, and CN1935268A disclose an alginate dressing containing nano-silver, which has good antimicrobial properties. However, published literatures show that nano-silver has some cytotoxicity.

Chinese patent CN103835025B discloses a technique for preparing an antimicrobial alginate fiber. The method is to provide sodium alginate to be reacted with a polymeric antimicrobial guanine, and then reacted with a mixture light rare earth elements, to obtain a polymer complex spinning mother liquid, and then a wet spinning process is performed to produce the antimicrobial alginate fiber. Because the method involves complexation between anionic alginate and cationic macromolecular polyguanidine, the technique requires a large amount of polyhexamethylene biguanide salt to be added. The macromolecular polyguanidine is easily dissolved in water, especially when it is present in a dressing as a thin film or fine particles, the macromolecular polyguanidine is almost instantly dissolved in water, which is potentially highly risky.

U.S. Pat. No. 8,921,427 discloses an antimicrobial preparation for preparing a wound dressing or bandage. The antimicrobial agents include biguanide derivatives, octetidine or methyldiazine apply the antimicrobial properties to the alginate by spraying or soaking. In some embodiments, the polyhexamethylene biguanide hydrochloride is loaded on calcium alginate fiber by a conventional soaking method, and loaded amounts in the embodiments are 0.5%, 1.0%, 1.5%, and 2.0%, respectively, and the antimicrobial property is evaluated by an agar diffusion method. The patent also provides an opinion that is contrary to the general view held by experts. According to the general view, when cationic polyhexamethylene biguanide hydrochloride is used, even a small amount of negatively charged molecules, such as alginate, acrylate, and lactate or iodide ions, can also quickly passivate the antimicrobial property. An antimicrobial evaluation model in the patent is problematic. The more reliable AATCC Test Method 100-2012 was not used for quantitative identification. It is well known that the correctness of expert opinions can be easily proved by a simple experimental design, such as a simple plate count, using sodium alginate solution as a neutralizing agent for polyhexamethylene biguanide hydrochloride. In addition, the polyhexamethylene biguanide hydrochloride loaded on the alginate is highly soluble in water by the conventional soaking method, and the technique requires a high level of polyhexamethylene biguanide hydrochloride (0.5%-10%) to be added, which is highly risky.

SUMMARY OF THE DISCLOSURE

In order to achieve good antimicrobial property of alginate dressings, and to ensure a sufficient safety factor for human bodies, the current antimicrobial alginate dressing technologies all have certain defects in related art.

In order to solve the above-mentioned technical problem, a technical solution adopted by the present disclosure is to provide an antimicrobial alginate fiber, including a molecular structure as shown in formula (1).

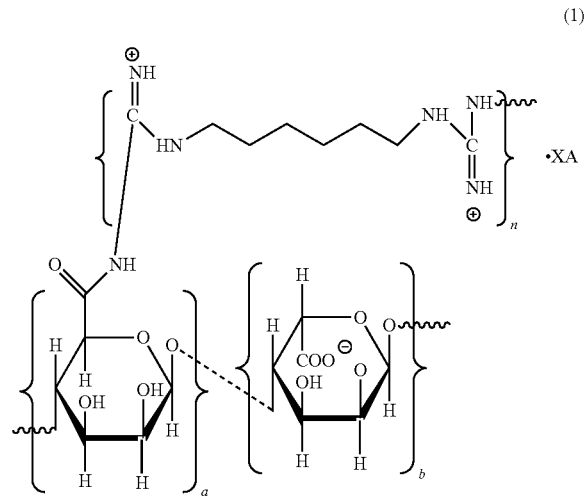

(1)

X may be equal to 10 to 40, n may be equal to 10 to 40, and A may be anyone of hydrochloric acid, phosphoric acid, propionic acid, and gluconic acid. In particular, number a and b are general descriptions of the molecular structure of alginate, and are not in specific numerically limited.

Further, the antimicrobial alginate fiber may be obtained by loading polyhexamethylene biguanide salt to an alginate fiber via an interfacial reaction with covalent bonding.

Further, the alginate may be one of water soluble alginates, one of water insoluble alginates, and a blend of the water soluble alginate and the water insoluble alginate; the water soluble alginate may be anyone of sodium alginate, potassium alginate, lithium alginate, magnesium alginate, and ammonium alginate; the water insoluble alginate may be anyone of calcium alginate and zinc alginate.

Further, the blend of the water soluble alginate and the water insoluble alginate may include blends formed of water soluble alginates with calcium ions or zinc ions as a cross-linking agent.

Further, the polyhexamethylene guanidine salt may be anyone and its derivative of polyhexamethylene guanide hydrochloride, polyhexamethylene biguanide hydrochloride, polyhexamethylene guanide phosphoric acid, polyhexamethylene biguanide phosphoric acid, polyhexamethylene guanide propionic acid, polyhexamethylene biguanide propionic acid, polyhexamethylene guanidine gluconate, and polyhexamethylene biguanidine gluconate. In particular, the mass of polyhexamethylene guanide salt may be in a range of 0.05% to 0.5%.

A method for manufacturing the above-mentioned antimicrobial alginate fiber dressing may include operations in the following blocks.

Block S1, aqueous hydrochloric acid or ethanol hydrochloride solution may be provided as an inorganic reaction phase, and chloroform solution is provided as an organic reaction phase; then a catalyst is added into the mixed solution, wherein activation time of an alginate fiber in the mixed solution may be 10 to 60 minutes, and the activation temperature may be 10 to 40° C.

Block S2, the alginate fiber treated in block S1 is added into antimicrobial active ethanol solution, wherein reaction time may be 0.5 to 24 hours, and the reaction temperature may be 10 to 40° C.; and the antimicrobial active ethanol solution is polyhexamethylene biguanide hydrochloride (PHMB×HCl) ethanol solution.

Block S3, the alginate fiber treated with antimicrobial active ethanol solution is added to the chloroform solution, wherein reaction time may be 0.5 to 24 hours, and the reaction temperature may be 10 to 40° C.

Block S4, polyhexamethylene biguanide hydrochloride is covalent bonded with the alginate fiber treated in block S3 in the interface of the alginate fiber treated in block S3, to form a molecular scaled polyhexamethylene biguanide hydrochloride coating layer. The reaction principle is shown in FIG. 1, and its structural illustration is shown in FIG. 2.

Block S5, the alginate fiber obtained in block S4 may be washed once by 10/10000~50/10000 sodium hydroxide alcohol solution, wherein the ethanol is at the concentration of 70%; then may be washed 3-6 times by 80% to 95% ethanol; and then washed 1-3 times, by absolute ethanol. Finally, the antimicrobial alginate fiber is obtained by vacuum drying in a vacuum pump at the temperature of 40 to 65° C. for 12 to 24 hours.

Further, In block S1, the aqueous hydrochloride may contain 0.1% (m/m) to 5.0% (m/m) of hydrochloric acid, and 85.0% (m/m) to 99.9% (m/m) of water, and a mass ratio of the hydrochloric aqueous solution to the alginate fiber may be 4.0 to 10.0; activation time of the alginate fiber in the mixed solution may be 0.5 to 24.0 hours, and the activation temperature may be 10 to 40° C. Further, in block S1, the ethanol hydrochloride solution may contain 0.5% (m/m) to 5.0% (m/m) of hydrochloric acid, 10% (m/m) to 30% (m/m) of water, and 70% (m/m) to 90% (m/m) of ethanol, and a mass ratio of the ethanol hydrochloride solution to the alginate fiber may be 4.0 to 10; activation time of the alginate fiber in the mixed solution may be 0.5 to 24 hours, and the activation temperature may be 10 to 40° C.

Further, the catalyst is a mixture of triphenylphosphine, iodine, and N,N-diisopropylethylamine; the triphenylphosphine and iodine are in equimolar ratio. A mass fraction of the triphenylphosphine in the chloroform solution may be 0.05% to 3.00%; a mass fraction of the iodine in the chloroform solution may be 0.05% to 3.00%; and a mass fraction of the N,N-diisopropylethylamine in the chloroform solution may be 0.5% to 8.0%.

The catalyst is prepared by pre-dissolving triphenylphosphine and iodine in chloroform to reach a desired concentration, and then pre-weighed N,N-diisopropylethylamine may be rapidly added to the solution under stirring at 50-100 r/min, and then the primary activated alginate fiber may be added.

Further, in block S1, a mass ratio of the mixed solution to the alginate fiber may be 4.0 to 20.0, the activation time of the alginate fiber in the mixed solution may be 10 to 60 minutes, and the activation temperature may be 10 to 40° C. Further, in block S2, mass concentration of the antimicrobial active ethanol solution may be at 0.01% to 5.00% (m/m), and the mass of the antimicrobial active ethanol solution may be 2 to 10 times of the mass of the alginate fiber.

The present disclosure may provide an application of the above-mentioned antimicrobial alginate fiber dressing. The antimicrobial alginate fiber may be processed by combing, laying, and needle-punching, to form alginate nonwoven fabrics; and the alginate nonwoven fabrics may be processed by cutting, packaging, and sterilizing, to form an antimicrobial alginate fiber dressing product, such as an antimicrobial alginate towel, antimicrobial alginate nonwoven fabrics, and antimicrobial alginate gauze; the antimicrobial alginate fiber dressing products may be applied to acute and chronic wound care.

In the present disclosure, the alginate dressings may have good wound care properties such as safety, non-toxicity, high hygroscopicity, hemostasis, gelation, and promoting wound healing. Polyhexamethylene biguanide hydrochloride is broad spectrum antimicrobial, highly effective and safe, and is considered to be a safe and non-toxic disinfectant. A new generation of antimicrobial dressings adopts polyhexamethylene biguanide hydrochloride as an antimicrobial agent to develop products, such as FortaDerm™ Antimicrobial PHMB Wound Dressing, COPA AMD dressings, CollaWound ART, PolyFIT+ Absorbing Antimicrobial Dressings, Kendall Kerlix AMD Antimicrobial Gauze Dressing, Suprasorb® X+PHMB Antimicrobial HydroBalance wound dressing, CelluDress-PHMB Medicareplus International.

Applications of polyhexamethylene biguanide hydrochloride (PHMB×HCl) in wound management are very mature. Compared with other antimicrobial agents such as chitosan, silver and iodine, it has special properties as the following.

(1) The polyhexamethylene biguanide hydrochloride is easily dissolved in water, especially in a form of thin films or fine particles in the dressing; it is almost instantly dissolved in water.

(2) The polyhexamethylene biguanide hydrochloride in an aqueous solution is a cationic polymer, and remains substantially cationic over a wide range of pH.

(3) When a human body absorbs a high level of the polyhexamethylene biguanide hydrochloride, it has potential carcinogenicity, potential mutagenicity, and potential reproductive toxicity (the new act issued by European Commission for Consumer Safety Science (SCCS) in April 2017 sets its safety limit to 0.1%).

Therefore, the above three special properties determine that the polyhexamethylene biguanide salt cannot be loaded with the alginate dressing by conventional methods such as soaking, spraying or painting. The reasons are as the following. (1) Alginate is an anionic polymer, and polyhexamethylene biguanide hydrochloride is a cationic polymer. These two polymers can undergo an ionic complexation reaction in an aqueous solution, which quickly passivates the antimicrobial function, so that it is necessary to add a large amount of polyhexamethylene biguanide salt. (2) The polyhexamethylene biguanide hydrochloride in the dressing dissolves rapidly in the wound exudation, and then quickly penetrates the wound cells, so that the concentration of the antimicrobial agent in the dressing decays under the minimal antimicrobial concentration in a short period of time, eventually losing the antimicrobial property. It cannot meet the demand of a long-term antimicrobial function for dressing. (3) A large amount of dissolved polyhexamethylene biguanide salt does not meet safety requirements.

Based on the above-mentioned reasons, by a large number of creative research experiments by Applicant, it was discovered and confirmed for the first time that when the alginate fiber is loaded to polyhexamethylene biguanidine salt under an interface reaction with covalent bonding, the antimicrobial activity of the material is not passivated. Instead, the antimicrobial activity has a further improvement over the original activity. The polyhexamethylene biguanide salt, which is interfacial bonded with the alginate dressing, has almost no dissolution, and only a small amount of polyhexamethylene biguanide salt is dissoluted due to the dissolve of some of the alginate. The discovery of the present disclosure may provide a strong technical rationale for the development of a new generation of alginate antimicrobial dressings.

Applications of polyhexamethylene guanide salt in wound management are very mature, and have been proven to positively promote wound healing and reduce pain, unpleasant smells and formation of carrion. The novel antimicrobial alginate dressing of the present disclosure is a polyhexamethylene guanide salt coating layer formed at the interface of alginate fibers. The novel antimicrobial alginate dressing of the present disclosure may solve the problem of combining the two materials of the alginate and the polyhexamethylene guanide salt, and reduces the potential safety risk of polyhexamethylene guanide salts, especially for the treatment of chronic wounds.

The present disclosure may solve the technical problem that when the cationic polymer polyhexamethylene guanide salt is mixed with the anionic polymer alginate, the antimicrobial activity of the polyhexamethylene guanide salt is quickly passivated. The present disclosure realizes that a low level of polyhexamethylene guanide salt alginate in the dressing performs good and long-term antimicrobial activities. The polyhexamethylene guanide salt has a low dissolution rate and is highly safe, and reduces a potential risk of carcinogenicity, mutagenicity and reproductive toxicity. The polyhexamethylene guanide salt may achieve technical effects as the following.

1. The interface of the alginate fiber may have a good antimicrobial effect with only a small amount of PHMB, and the mass percentage of the PHMB is 0.05% to 0.50%.

2. The antimicrobial property is good, and can be maintained for a long time up to 7 to 14 days. Requirements of the ideal modern wound dressing antimicrobial property can be met.

DETAILED DESCRIPTION

An optimal embodiment of the antimicrobial alginate fiber includes a molecular structure as shown following.

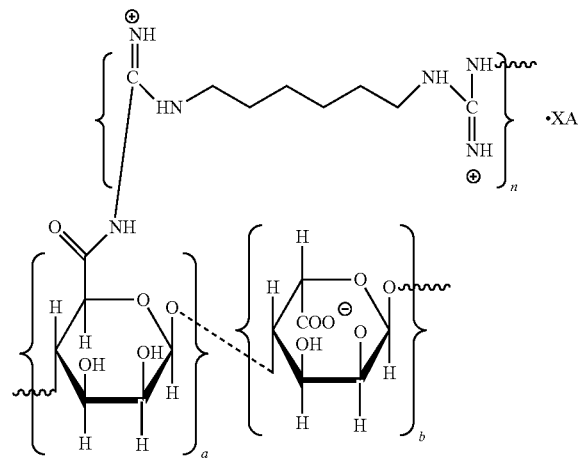

X is equal to 30, n is equal to 30, and A is propionic acid. Number a and b are general descriptions of the molecular structure of alginate, and are not in specific numerically limited.

Further, the antimicrobial alginate fiber is obtained by loading polyhexamethylene biguanide to an alginate fiber via an interfacial reaction with covalent bonding.

Further, the alginate is selected from one of water soluble alginates, water insoluble alginates, and a blend of a water soluble alginate and a water insoluble alginate. The water soluble alginate is ammonium alginate. The water insoluble alginate is calcium alginate.

Further, the blend of the water soluble alginate and the water insoluble alginate includes blends formed of water soluble alginates with calcium ions as a crosslinking agent.

Further, the polyhexamethylene guanide salt is polyhexamethylene guanide gluconate and a derivative thereof. The mass of polyhexamethylene guanide salt is of 0.3% (m/m).

A method for manufacturing the above-mentioned antimicrobial alginate fiber dressing includes operations in the following steps.

Block S1, aqueous hydrochloric acid or ethanol hydrochloride solution is provided as an inorganic reaction phase, and chloroform solution is provided as an organic reaction phase. Catalyst is added into the mixed solution. Activation time of an alginate fiber in the mixed solution is 35 minutes, and an activation temperature is 29° C.

Block S2, the alginate fiber treated in block S1 is added into antimicrobial active ethanol solution. Reaction time is 12 hours, and the reaction temperature is 29° C. The antimicrobial active ethanol solution is polyhexamethylene biguanide hydrochloride (PHMB×HCl) ethanol solution.

Block S3, the alginate fiber treated in block S2 is added into chloroform solution. Reaction time is 12 hours, and the reaction temperature is 29° C.

Figure 1:
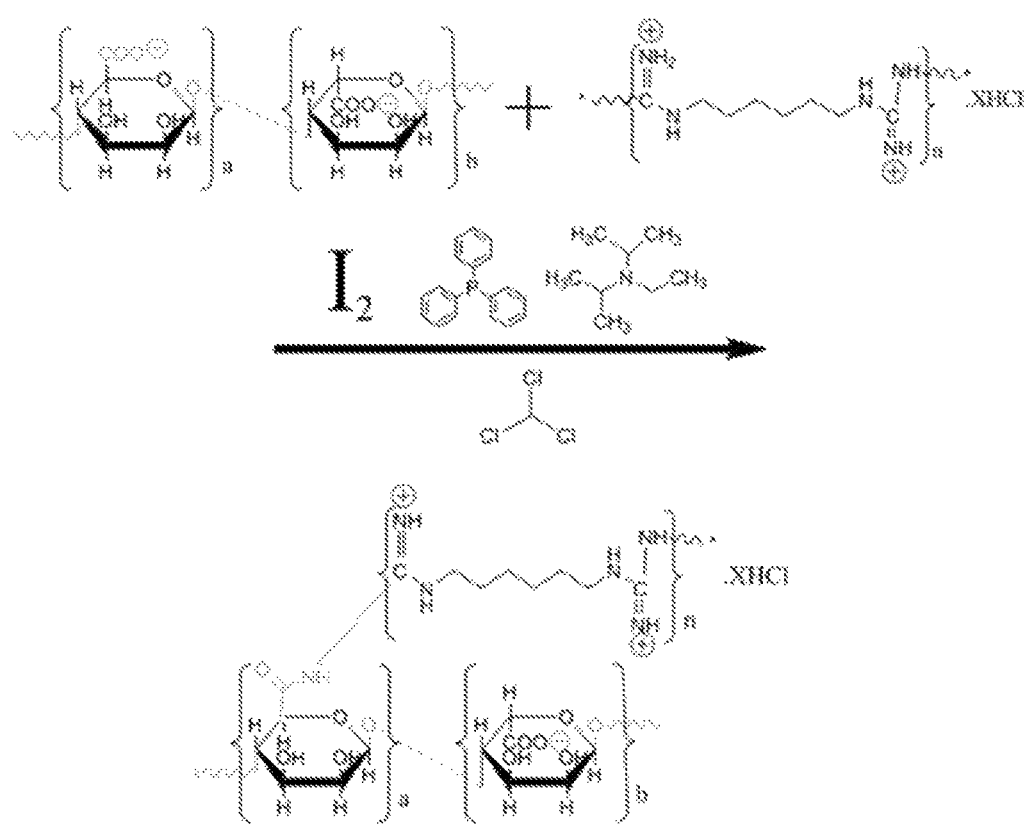
FIG. 1 is an illustration of a reaction process in the present disclosure.
Figure 2:
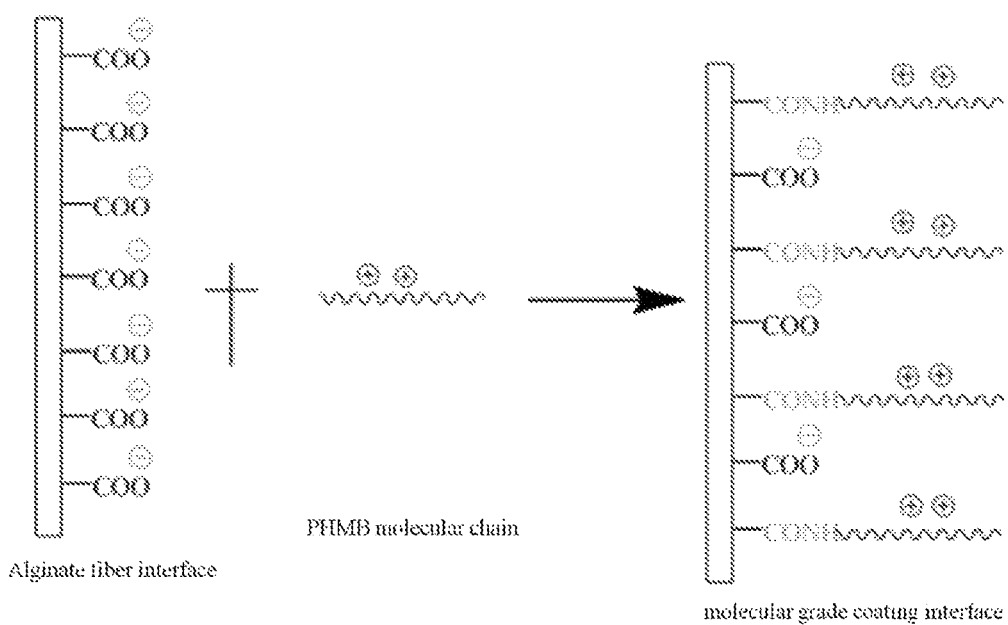
FIG. 2 is an illustration of an interface structure of an alginate fiber and polyhexamethylene biguanide salt.

Block S4, the alginate fiber treated in block S3 has an interfacial reaction with polyhexamethylene biguanide hydrochloride with covalent bonding, forming a molecular scaled polyhexamethylene biguanide hydrochloride coating layer. The reaction principle is shown in FIG. 1, and its structural illustration is shown in FIG. 2.

Block S5, the alginate fiber obtained in block S4 is washed once by 40/10000 sodium hydroxide ethanol solution, the ethanol is at the concentration of 70%. The alginate fiber is then washed 4 times by 85% ethanol, and then washed twice by absolute ethanol. The antimicrobial alginate fiber is obtained by vacuum drying in a vacuum pump, for 20 hours at 55° C.

Further, in block S1, the aqueous hydrochloric acid solution contains 1% (m/m) of hydrochloric acid, and 99% (m/m) of water. A mass ratio of the aqueous hydrochloric acid solution to the alginate fiber is 7.0. Activation time of the alginate fiber in the mixed solution is 12 hours, and the activation temperature is 29° C. Further, in block S1, the ethanol hydrochloride solution contains 3% (m/m) of hydrochloric acid, 25% (m/m) of water, and 72% (m/m) of ethanol, and a mass ratio of the ethanol hydrochloride solution to the alginate fiber is 7.0. Activation time of the alginate fiber in the mixed solution is 12 hours, and the activation temperature is 29° C.

Further, the catalyst is a mixture of triphenylphosphine, iodine, and N,N-diisopropylethylamine. The triphenylphosphine and iodine is in equimolar ratio. The mass fraction of triphenylphosphine in the chloroform solution is 1.8%. The mass fraction of iodine in the chloroform solution is 1.8%. The mass fraction of N,N-diisopropylethylamine in the chloroform solution is 4.5%.

The catalyst is prepared by pre-dissolving triphenylphosphine and iodine in chloroform to reach a desired concentration, and then pre-weighed N,N-diisopropylethylamine is rapidly added into the solution with stirring at 90 r/min, and then a primary activated alginate fiber is added.

Further, in block S1, a mass ratio of the mixed solution to the alginate fiber is 18. The activation time of the alginate fiber in the mixed solution is 25 minutes, and the activation temperature is 29° C. Further, in block S2, the concentration of the antimicrobial active ethanol solution is 2.5% (m/m), and the mass of the antimicrobial active ethanol solution is 5 times of the mass of the alginate fiber.

EMBODIMENTS OF THE PRESENT DISCLOSURE

Embodiment 1

A method is provided for manufacturing an antimicrobial alginate fiber dressing. A short alginate fiber with length of 3 to 5 cm is provided with 1000 g, and is placed into 5000 g of aqueous solution containing 0.54% of hydrochloric acid and 9.5% of ethanol, at 20° C. The solution with the alginate fiber is stirred and activated for 3.0 hours, and then the alginate fiber is separated from the aqueous solution by centrifuge. The alginate fiber may be soaked with 2000 g of absolute ethanol for 10 to 15 minutes, and then ethanol is separated by centrifuge to obtain a primary activated alginate fiber. 110 g of N,N-diisopropylethylamine is added into 5500 g of chloroform solution (triphenylphosphine: 0.235%, and iodine: 0.228%) with stirring at 70 r/min, and the stirring time is counted by a timer. After stirring for 1-2 minutes, the primary activated alginate fiber is put into the chloroform solution. The chloroform solution may be stirred for 3 to 5 minutes, and then is activated at 35° C. for 30 minutes. The solution is separated by pressing to obtain a secondary activated fiber. Next, 4000 g of PHMB ethanol solution where PHMB is at 0.028% (m/m) and the secondary activated fiber is mixed and stirred at 25° C. for 40 minutes. The secondary activated fiber is separated from the PHMB ethanol solution by pressing to remove liquid, and is placed in the previous chloroform solution with stirring at 25° C. for 4 hours. Liquid is separated by centrifuge to obtain a PHMB coated alginate fiber. Finally, the PHMB coated alginate fiber is washed once by 15/10000 sodium hydroxide ethanol solution (ethanol at concentration of 70%), then washed by 95% ethanol for 4 times, then washed once by absolute ethanol, and may be dried at 55° C. by vacuum for 24 hours to obtain 925 g of semi-finished product. The alginate fiber, which is covalent bonded with PHMB in the interface, is subjected to needling and hot press drying process. Alginate nonwoven fabrics is obtained by combing, laying, and needle punching, and then is cut, packaged, and sterilized.

A nonwoven antimicrobial alginate dressing containing 0.056% of PHMB is obtained, and the weight of the dressing is 148 g/m².

Embodiment 2

A method is for manufacturing an antimicrobial alginate fiber dressing. A short alginate fiber with length of 3 to 5 cm may be provided with 1000 g, and is placed into 5000 g of aqueous solution containing 0.54% of hydrochloric acid and 9.5% of ethanol, at 20° C. The alginate fiber in the aqueous solution is stirred and activated for 3.0 hours, and then the alginate fiber is separated from the aqueous solution by centrifuge. The fiber alginates may be then soaked with 2000 g of absolute ethanol for 10 to 15 minutes, and the ethanol is separated by centrifuge to obtain a primary activated alginate fiber. 110 g of N,N-diisopropylethylamine is added into 5500 g of chloroform solution (triphenylphosphine: 0.235%, and iodine: 0.228%) with stirring at 70 r/min, and the stirring time is counted by a timer. After stirring for 1-2 minutes, the primary activated alginate fiber is placed into the chloroform solution. The alginate fiber in the chloroform solution is stirred for 3 to 5 minutes, and activated at 35° C. for 30 minutes. The fiber is taken out of the solution, and is compressed to remove remaining liquid, obtaining a secondary activated fiber. Next, 4000 g of PHMB ethanol solution where PHMB is at a concentration of 0.038% (m/m) and the secondary activated fiber is mixed and stirred at 25° C. for 40 minutes. The secondary activated fiber is separated from the PHMB ethanol solution by pressing to remove liquid, and placed in the previous chloroform solution with stirring at 25° C. for 4 hours. Liquid is separated by centrifuge to obtain a PHMB coated alginate fiber. Finally, the PHMB coated alginate fiber is washed once by 15/10000 sodium hydroxide alcohol solution (alcohol at concentration of 70%), then washed by 95% alcohol for 4 times, then washed once by absolute ethanol, and is dried at 55° C. by vacuum for 24 hours to obtain 941 g of semi-finished product. The alginate fiber, which is covalent bonded with PHMB in the interface, is subjected to needling and hot press drying process. Alginate nonwoven fabrics is obtained by combing, laying, and needle punching, and then is cut, packaged, and sterilized.

A nonwoven antimicrobial alginate dressing containing 0.076% of PHMB is obtained, and the weight of the dressing is 136 g/m².

Embodiment 3

A method is for manufacturing an antimicrobial alginate fiber dressing. A long alginate fiber is provided with 1000 g, and is placed into 5000 g of aqueous solution containing 0.54% of hydrochloric acid and 9.5% of ethanol, at 20° C. The alginate fiber in the aqueous solution is stirred and activated for 3.0 hours, and then the alginate fiber is separated from the aqueous solution by centrifuge to remove liquid. The alginate fiber may be soaked with 2000 g of absolute ethanol for 10 to 15 minutes, and then ethanol is separated by centrifuge to obtain a primary activated alginate fiber. 110 g of N,N-diisopropylethylamine is added into 5500 g of chloroform solution (triphenylphosphine: 0.235%, and iodine: 0.228%) with stirring at 70 r/min, and the stirring time is counted by a timer. After stirring for 1-2 minutes, the primary activated alginate fiber is placed into the chloroform solution. The chloroform solution is stirred for 3 to 5 minutes, and then the primary activated alginate fiber is activated at 35° C. for 30 minutes. The fiber is then taken out of the solution, and is compressed to remove remaining liquid, to obtain a secondary activated fiber. Next, 4000 g of PHMB ethanol solution where PHMB is at the concentration of 0.052% (m/m) and the secondary activated fiber is mixed and stirred at 25° C. for 40 minutes. The secondary activated fiber is separated from the PHMB ethanol solution by pressing to remove liquid, and is placed in the previous chloroform solution with stirring at 25° C. for 4 hours. Liquid is separated by centrifuge to obtain a PHMB coated alginate fiber. Finally, the PHMB coated alginate fiber is washed once by 15/10000 sodium hydroxide alcohol solution (alcohol at the concentration of 70%), then washed by 95% alcohol for 4 times, then washed once by absolute ethanol, and then dried at 55° C. by vacuum for 24 hours to obtain 930 g of semi-finished product. The long alginate fiber, which is covalent bonded with PHMB in the interface, is processed to obtain gauze, which is then cut, packaged, and sterilized.

A gauze antimicrobial alginate dressing containing 0.115% of PHMB is obtained, and the weight of the dressing is 167 g/m².

Embodiment 4

A method is for manufacturing an antimicrobial alginate fiber dressing. A short alginate fiber with length of 3 to 5 cm may be provided with 1000 g, and is placed into 5000 g of aqueous solution containing 0.54% of hydrochloric acid and 9.5% of ethanol, at 20° C. The alginate fiber in the aqueous solution is stirred and activated for 3.0 hours, and then the alginate fiber is separated from the aqueous solution by centrifuge to remove liquid. The alginate fiber may be soaked with 2000 g of absolute ethanol for 10 to 15 minutes, and then ethanol is separated by centrifuge to obtain a primary activated alginate fiber. 110 g of N,N-diisopropylethylamine is added into 5500 g of chloroform solution (triphenylphosphine: 0.235%, and iodine: 0.228%) with stirring at 70 r/min, and stirring time is counted by a timer. After stirring for 1-2 minutes, the primary activated alginate fiber is placed into the chloroform solution. The chloroform solution is stirred for 3 to 5 minutes, and the primary activated alginate fiber is activated at 35° C. for 30 minutes. The fiber is taken out of the solution, and is compressed to remove remaining liquid, to obtain a secondary activated fiber. Next, 4000 g of PHMB ethanol solution where PHMB is at the concentration of 0.082% (m/m) and the secondary activated fiber is mixed and stirred at 25° C. for 40 minutes. The secondary activated fiber is separated from the PHMB ethanol solution by pressing to remove liquid, and is placed in the previous chloroform solution with stirring at 25° C. for 4 hours. Liquid is separated by centrifuge to obtain a PHMB coated alginate fiber. Finally, the PHMB coated alginate fiber is washed once by 15/10000 sodium hydroxide alcohol solution (alcohol at the concentration of 70%), then washed by 95% alcohol for 4 times, then washed once by absolute ethanol, and is dried at 55° C. by vacuum for 24 hours to obtain 921 g of semi-finished product. The alginate fiber, which is covalent bonded with PHMB in the interface, is subjected to needling and hot press drying process. Alginate nonwoven fabrics is obtained by combing, laying, and needle punching, and then is cut, packaged, and sterilized.

A nonwoven antimicrobial alginate dressing containing 0.181% of PHMB is obtained, and the weight of the dressing is 145 g/m².

Embodiment 5

A method is for manufacturing an antimicrobial alginate fiber dressing. A short alginate fiber with length of 3 to 5 cm may be provided with 1000 g, and is placed into 5000 g of aqueous solution containing 0.54% of hydrochloric acid and 9.5% of ethanol, at 20° C. The aqueous solution is stirred and activated for 3.0 hours, and then the alginate fiber is separated from the aqueous solution by centrifuge to remove liquid. The alginate fiber may be soaked with 2000 g of absolute ethanol for 10 to 15 minutes, and then ethanol is separated by centrifuge to obtain a primary activated alginate fiber. 110 g of N,N-diisopropylethylamine is added into 5500 g of chloroform solution (triphenylphosphine: 0.235%, and iodine: 0.228%) with stirring at 70 r/min, and stirring time is counted by a timer. After stirring for 1-2 minutes, the primary activated alginate fiber is placed into the chloroform solution. The chloroform solution may be stirred for 3 to 5 minutes, and the primary activated alginate fiber is activated at 35° C. for 30 minutes. The fiber is taken out of the solution and is compressed to remove remaining liquid, to obtain a secondary activated fiber. Next, 4000 g of PHMB ethanol solution where PHMB is at the concentration of 0.104% (m/m) and the secondary activated fiber is mixed and stirred at 25° C. for 40 minutes. The secondary activated fiber is separated from the PHMB ethanol solution by pressing to remove liquid, and is placed in the previous chloroform solution with stirring at 25° C. for 4 hours. Liquid is separated from the chloroform solution by centrifuge to obtain a PHMB coated alginate fiber. Finally, the PHMB coated alginate fiber is washed once by 15/10000 sodium hydroxide alcohol solution (alcohol at the concentration of 70%), then washed by 95% of alcohol for 4 times, then washed once by absolute ethanol, and is dried at 55° C. by vacuum for 24 hours to obtain 925 g of semi-finished product. The alginate fiber, which is covalent bonded with PHMB in the interface, is subjected to needling and hot press drying process. Alginate nonwoven fabrics is obtained by combing, laying, and needle punching, and then cut, packaged, and sterilized.

A nonwoven antimicrobial alginate dressing containing 0.249% of PHMB is obtained, and the weight of the dressing is 119 g/m².

Embodiment 6

A method is for manufacturing an antimicrobial alginate fiber dressing. A short alginate fiber with length of 3 to 5 cm may be provided with 1000 g, and is placed into 5000 g of aqueous solution containing 0.54% of hydrochloric acid and 9.5% of ethanol, at 20° C. The aqueous solution is stirred and activated for 3.0 hours, and then the alginate fiber is separated from the aqueous solution by centrifuge to remove liquid. The alginate fiber may be soaked with 2000 g of absolute ethanol for 10 to 15 minutes, and then ethanol is separated by centrifuge to obtain a primary activated alginate fiber. 110 g of N,N-diisopropylethylamine is added into 5500 g of chloroform solution (triphenylphosphine: 0.235%, and iodine: 0.228%) with stirring at 70 r/min, and stirring time is counted by a timer. After stirring for 1-2 minutes, the primary activated alginate fiber is placed into the chloroform solution. The chloroform solution is stirred for 3 to 5 minutes, and the primary activated alginate fiber is activated at 35° C. for 30 minutes. The fiber is taken out of the solution and is compressed to remove remaining liquid, to obtain a secondary activated fiber. Next, 4000 g of PHMB ethanol solution where PHMB is at the concentration of 0.183% (m/m) and the secondary activated fiber is mixed and stirred at 25° C. for 40 minutes. The secondary activated fiber is separated from the PHMB ethanol solution by pressing to remove liquid, and is placed in the previous chloroform solution with stirring at 25° C. for 4 hours. Liquid is separated from the chloroform solution by centrifuge to obtain a PHMB coated alginate fiber. Finally, the PHMB coated alginate fiber is washed once by 15/10000 sodium hydroxide alcohol solution (alcohol at the concentration of 70%), then washed by 95% alcohol for 4 times, then washed once by absolute ethanol, and is dried at 55° C. by vacuum for 24 hours to obtain 918 g of semi-finished product. The alginate fiber, which is covalent bonded with PHMB in the interface, is subjected to needling and hot press drying process. Alginate nonwoven fabrics is obtained by combing, laying, and needle punching, and then cut, packaged, and sterilized.

A nonwoven antimicrobial alginate dressing containing 0.512% of PHMB is obtained and the weight of the dressing is 107 g/m².

Embodiment 7

An antimicrobial alginate fiber may include a molecular structure as shown following.

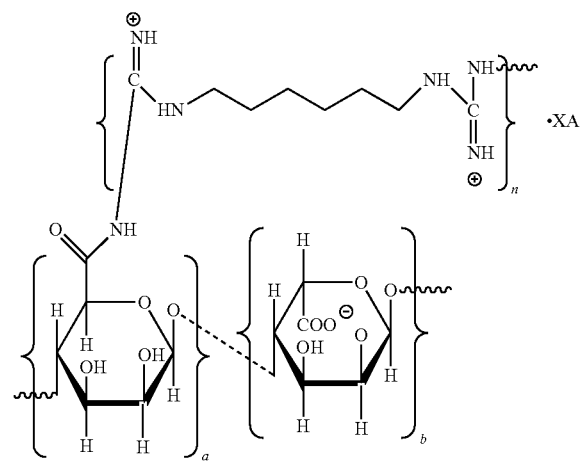

X is equal to 10, n is equal to 10, and A is hydrochloric acid. Numbers a and b are general descriptions of the molecular structure of alginate, and are not in specific numerically limited.

Further, the antimicrobial alginate fiber is obtained by loading polyhexamethylene biguanide salt to an alginate fiber via covalent bond formed by interfacial reaction.

Further, the alginate may be one of water soluble alginate, water insoluble alginate, and a blend of a water soluble alginate and a water insoluble alginate. The water soluble alginate is sodium alginate. The water insoluble alginate is calcium alginate.

Further, the blend of the water soluble alginate and the water insoluble alginate may include blends formed of water soluble alginate with calcium ions as a crosslinking agent.

Further, the polyhexamethylene guanide salt is polyhexamethylene guanidine hydrochloride and a derivative thereof. The polyhexamethylene guanide salt has a mass percentage of 0.5%.

A method for manufacturing the above-mentioned antimicrobial alginate fiber dressing includes operations in the following blocks.

Block S1, aqueous hydrochloric acid solution or ethanol hydrochloride solution is provided as an inorganic reaction phase, and chloroform solution is provided as an organic reaction phase. Catalyst is added into the mixed solution. Activation time of an alginate fiber in the mixed solution is 10 minutes, and an activation temperature is 10° C.

Block S2, the alginate fiber treated in block S1 is added into antimicrobial active ethanol solution. Reaction time is 0.5 hours, and the reaction temperature is 10° C. The antimicrobial active ethanol solution is polyhexamethylene biguanide hydrochloride (PHMB×HCl) ethanol solution.

Block S3, the alginate fiber treated in block S2 is added into chloroform solution. Reaction time is 0.5 hours, and the reaction temperature is 10° C.

Block S4, the alginate fiber treated in block S3 is covalent bonded with polyhexamethylene biguanide hydrochloride in the interface, forming a molecular scaled polyhexamethylene biguanide hydrochloride coating layer. The reaction principle is shown in FIG. 1, and its structural illustration is shown in FIG. 2.

Block S5, the alginate fiber obtained in block S4 is washed once by 10/10000 sodium hydroxide alcohol solution and the alcohol is at the concentration of 70%. The alginate fiber is then washed 6 times by 80% alcohol, and then washed once by absolute ethanol. The alginate fiber is then dried by a vacuum pump at 40° C. for 12 hours, to obtain the antimicrobial alginate fiber.

Further, in block S1, the aqueous hydrochloric acid solution contains 0.1% (m/m) of hydrochloric acid, and 99.9% (m/m) of water. A mass ratio of the aqueous hydrochloric acid solution to the alginate fiber is 4.0. The alginate fiber is activated in the mixed solution for 0.5 hours at 10° C. Further, in block S1, the ethanol hydrochloride solution contains 0.5% (m/m) of hydrochloric acid, 10% (m/m) of water, and 89.5% (m/m) of ethanol. A mass ratio of the ethanol hydrochloride solution to the alginate fiber mass ratio is 4.0. Activation time of the alginate fiber in the mixed solution is 0.5 hours, and the activation temperature is 10° C.

Further, the catalyst is a mixture of triphenylphosphine, iodine, and N,N-diisopropylethylamine. The triphenylphosphine and iodine is in equimolar ratio. The chloroform solution may contain 0.05% (m/m) of triphenylphosphine, 0.05% (m/m) of iodine, and 0.5 (m/m) of N,N-diisopropylethylamine.

The catalyst is prepared by pre-dissolving triphenylphosphine and iodine in chloroform to reach a desired concentration, and then pre-weighed N,N-diisopropylethylamine is rapidly added under stirring at 50 r/min, and then a primary activated alginate fiber is added.

Further, in block S1, a mass ratio of the mixed solution to the alginate fiber is 4.0. The activation time of the alginate fiber in the mixed solution is 10 minutes, and the activation temperature is 10° C. Further, in block S2, mass concentration of the antimicrobial active ethanol solution is 0.01%, and the mass of the antimicrobial active ethanol solution is 2 times of the mass of the alginate fiber.

An application of the above-mentioned antimicrobial alginate fiber dressing is provided. The above-mentioned antimicrobial alginate fiber may be processed by combing, laying, and needle-punching, to produce alginate nonwoven fabrics. The alginate nonwoven fabrics may be processed by cutting, packaging, and sterilizing, to produce an antimicrobial alginate fiber dressing product, such as an antimicrobial alginate towel, antimicrobial alginate nonwoven fabrics, and antimicrobial alginate gauze. The antimicrobial alginate fiber dressing product may be applied to acute and chronic wound care.

Embodiment 8

An antimicrobial alginate fiber includes a molecular structure as shown following.

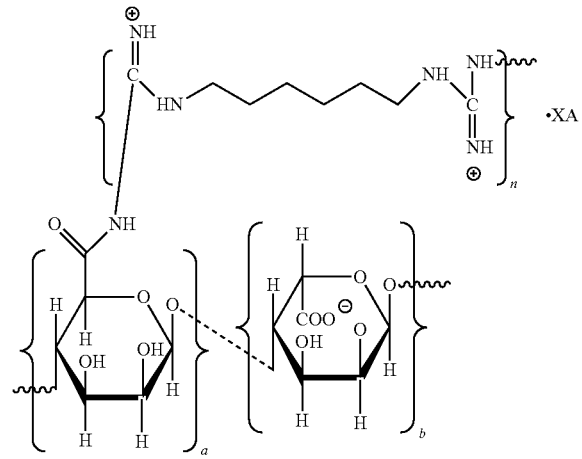

X is equal to 40, n is equal to 40, and A is gluconic acid. Number a and b are general descriptions of the molecular structure of alginate, and not in specific numerically limited.

Further, the antimicrobial alginate fiber is obtained by loading polyhexamethylene biguanide salt to an alginate fiber via covalent bond formed by interfacial reaction.

Further, the alginate may be one of water soluble alginate, one of water insoluble alginate, and a blend of a water soluble alginate and a water insoluble alginate. The water soluble alginate is magnesium alginate. The water insoluble alginate is zinc alginate.

Further, the blend of the water soluble alginate and the water insoluble alginate includes blends formed of water soluble alginate with zinc ions as a crosslinking agent.

Further, the polyhexamethylene guanide salt is polyhexamethylene guanide phosphoric acid and a derivative thereof. The polyhexamethylene guanide salt is in a mass percentage of 0.05%.

A method for manufacturing the above-mentioned antimicrobial alginate fiber dressing includes operations in the following blocks.

Block S1, aqueous hydrochloric acid solution or ethanol hydrochloride solution may be provided as an inorganic reaction phase, and chloroform solution is provided as an organic reaction phase. Catalyst is added into the mixed solution. Activation time of an alginate fiber in the mixed solution is 60 minutes, and an activation temperature is 40° C.

Block S2, the alginate fiber treated in block S1 is added into antimicrobial active ethanol solution. Reaction time is 24 hours, and the reaction temperature is 40° C. The antimicrobial active ethanol solution is polyhexamethylene biguanide hydrochloride (PHMB×HCl) ethanol solution.

Block S3, the alginate fiber treated in block S2 is added into chloroform solution. Reaction time is 24 hours, and the reaction temperature is 40° C.

Block S4, the alginate fiber treated in block S3 is covalent bonded with polyhexamethylene biguanide hydrochloride in the interface, to form a molecular scaled polyhexamethylene biguanide hydrochloride coating layer. The reaction principle is shown in FIG. 1, and its structural illustration is shown in FIG. 2.

Block S5, the alginate fiber obtained in block S4 is washed once by 50/10000 sodium hydroxide alcohol solution and the alcohol is at the concentration of 70%. The alginate fiber is then washed 3 times by 95% alcohol, and then washed 3 times by absolute ethanol. The alginate fiber is dried by a vacuum pump at 65° C. for 24 hours, to obtain the antimicrobial alginate fiber.

Further, in block S1, the aqueous hydrochloric acid solution contains 5.0% (m/m) of hydrochloric acid, and 85.0% (m/m) of water. A mass ratio of the aqueous hydrochloric acid solution to the alginate fiber is 10.0. Activation time of the alginate fiber in the mixed solution is 24 hours, and the activation temperature is 40° C.

Further, the catalyst is a mixture of triphenylphosphine, iodine, and N,N-diisopropylethylamine. The triphenylphosphine and iodine is in equimolar ratio. The chloroform solution contains 3.0% (m/m) of triphenylphosphine, 3.0% (m/m) of iodine, and 8.0% of N,N-diisopropylethylamine.

The catalyst is prepared by pre-dissolving triphenylphosphine and iodine in chloroform to reach a desired concentration, and then pre-weighed N,N-diisopropylethylamine is rapidly added under stirring at 100 r/min, and then a primary activated alginate fiber is added.

Further, in block S1, a mass ratio of the mixed solution to the alginate fiber is 20.0. The activation time of the alginate fiber in the mixed solution is 60 minutes, and the activation temperature is 40° C. Further, in block S2, mass concentration of the antimicrobial active ethanol solution is at 5.0%, and the mass of the antimicrobial active ethanol solution is 10 times of the mass of the alginate fiber.

An application of the above-mentioned antimicrobial alginate fiber dressing is provided. The antimicrobial alginate fiber is processed by combing, laying, and needle-punching, to form an alginate nonwoven. The alginate nonwoven is processed by cutting, packaging, and sterilizing, to form an antimicrobial alginate fiber dressing product, such as an antimicrobial alginate towel, an antimicrobial alginate nonwoven fabrics, and antimicrobial alginate gauze. The antimicrobial alginate fiber dressing product may be applied to acute and chronic wound care.

Embodiment 9

An antimicrobial alginate fiber includes a molecular structure as shown following.

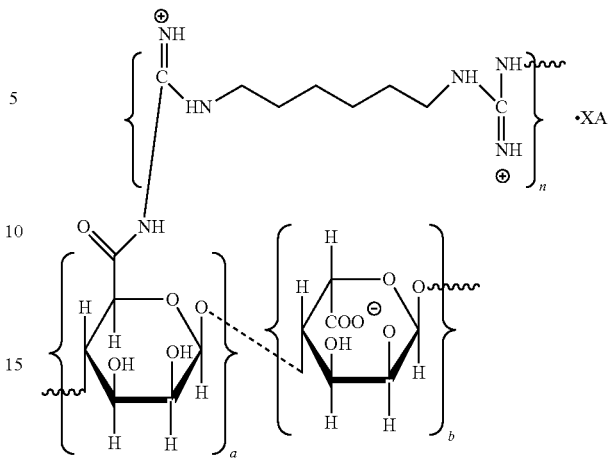

X is equal to 20, n is equal to 20, and A is phosphoric acid. Number a and b are general descriptions of the molecular structure of alginate, and not in specific numerically limited.

Further, the antimicrobial alginate fiber is obtained by loading polyhexamethylene biguanide to an alginate fiber via covalent bond formed by interfacial reaction.

Further, the alginate may be one of water soluble alginate, one of water insoluble alginate, and a blend of the water soluble alginate and the water insoluble alginate. The water soluble alginate is potassium alginate. The water insoluble alginate is calcium alginate.

Further, the blend of the water soluble alginate and the water insoluble alginate includes blends formed of water soluble alginate with calcium ions as a crosslinking agent.

Further, the polyhexamethylene guanide salt is polyhexamethylene propionate and a derivative thereof. The polyhexamethylene guanide salt is at the concentration of 0.5% (m/m).

A method for manufacturing the above-mentioned antimicrobial alginate fiber dressing includes operations in the following blocks.

Block S1, aqueous hydrochloric acid solution or ethanol hydrochloride solution is provided as an inorganic reaction phase, and chloroform solution is provided as an organic reaction phase. Catalyst is added into the mixed solution. Activation time of an alginate fiber in the mixed solution is 30 minutes, and an activation temperature is 25° C.

Block S2, the alginate fiber treated in block S1 is added into antimicrobial active ethanol solution. Reaction time is 8 hours, and the reaction temperature is 25° C. The antimicrobial active ethanol solution is polyhexamethylene biguanide hydrochloride (PHMB×HCl) ethanol solution.

Block S3, the alginate fiber treated in block S2 is added into chloroform solution. Reaction time is 8 hours, and the reaction temperature is 25° C.

Block S4, the alginate fiber treated in block S3 is covalent bonded with polyhexamethylene biguanide hydrochloride in the interface, to form a molecular scaled polyhexamethylene biguanide hydrochloride coating layer. The reaction principle is shown in FIG. 1, and its structural illustration is shown in FIG. 2.

Block S5, the alginate fiber obtained in block S4 is washed once by 30/10000 sodium hydroxide alcohol solution and the alcohol is at the concentration of 70%. The alginate fiber is then washed 5 times by 90% alcohol, and then washed twice by absolute ethanol. The alginate fiber is dried by a vacuum pump at 50° C. for 18 hours, to obtain the antimicrobial alginate fiber.

Further, in block S1, the aqueous hydrochloric acid solution contains 2.0% (m/m) of hydrochloric acid, and 88% (m/m) of water. A mass ratio of the aqueous hydrochloric acid solution to the alginate fiber is 6.0. Activation time of the alginate fiber in the mixed solution is 8 hours, and the activation temperature is 25° C. Further, in block S1, the ethanol hydrochloric acid solution contains 2% (m/m) of hydrochloric acid, 20% (m/m) of water, and 78% (m/m) of ethanol, and a mass ratio of the ethanol hydrochloride solution to the alginate fiber is 6. Activation time of the alginate fiber in the mixed solution is 8 hours, and the activation temperature is 25° C.

Further, the catalyst is a mixture of triphenylphosphine, iodine, and N,N-diisopropylethylamine. The triphenylphosphine and iodine is in equimolar ratio. A mass fraction of the triphenylphosphine in the chloroform solution is 1.0%. A mass fraction of the iodine in the chloroform solution is 1.0%. A mass fraction of the N,N-diisopropylethylamine in the chloroform solution the N,N-diisopropylethylamine is 3.0%.

The catalyst is prepared by pre-dissolving triphenylphosphine and iodine in chloroform to reach a desired concentration, and then pre-weighed N,N-diisopropylethylamine is rapidly added under stirring at 80 r/min, and then a primary activated alginate fiber is added.

Further, in block S1, a mass ratio of the mixed solution to the alginate fiber is 6.0. The activation time of the alginate fiber in the mixed solution is 30 minutes, and the activation temperature is 25° C. Further, in block S2, mass concentration of the antimicrobial active ethanol solution is at 2.0%, and the mass of the antimicrobial active ethanol solution is 6 times of the mass of the alginate fiber.

An application of the above-mentioned antimicrobial alginate fiber dressing is provided. An antimicrobial alginate fiber may be processed by combing, laying, and needle-punching, to form an alginate nonwoven. The alginate nonwoven may be processed by cutting, packaging, and sterilizing, to form an antimicrobial alginate fiber dressing product, such as an antimicrobial alginate towel, an antimicrobial alginate nonwoven fabrics, and antimicrobial alginate gauze. The antimicrobial alginate fiber dressing product may be applied to acute and chronic wound care.

Antimicrobial effect tests of embodiments are provided in the present disclosure.

1. An antimicrobial property test may be performed as the following description.

The quantitative evaluation method of antimicrobial activity refers to "AATCC 100-2012 Antimicrobial Finishes on Textile Materials Assessment of Fulltext Information", which is briefly described as the following description.

(1) Test strains: Gram-positive bacteria, *Enterococcus faecalis* (ATCC 51575); Gram-negative bacteria, *Pseudomonas aeruginosa* (ATCC 9027).

(2) Medium: nutrient broth, and agar medium (NB, NA).

(3) Diluent: sterile phosphate buffered saline (PBS).

(4) Simulated wound fluid (SWF): PBS containing 10% (V/V) fetal bovine serum.

(5) Live bacteria concentration: $2 \times 10^6$ cfu/ml to $4 \times 10^6$ cfu/ml.

(6) Test sample: a circular alginate dressing with a diameter of 4.8 cm±0.1 cm (1.9±0.03 inches).

(7) Inoculum: PBS containing 1.0±0.1 ml 10% (V/V) fetal bovine serum, and live bacteria concentration $2 \times 10^6$ cfu/ml to $4 \times 10^6$ cfu/ml.

(8) Neutralizing reagent: lecithin at the concentration of 20 g/L, 100 ml of TPS solution containing 20 g/L of Tween-80.

(9) Antimicrobial period: 24 hours, 7 days/168 hours, and 14 days/336 hours.

The test results are shown in the following table.

| Strains | Sample | Content of PHMB (%) | Antimicrobial rate in 24 hours (%) | Antimicrobial rate in 7 days (%) | Antimicrobial rate in 14 days (%) |
|---|---|---|---|---|---|
| *Enterococcus faecalis* | Embodiment 1 | 0.056 | — | 99.5 | 99.7 |
| | Embodiment 2 | 0.076 | 99.96 | 99.99 | 99.99 |
| | Embodiment 3 | 0.115 | 99.99 | 100 | 100 |
| | Embodiment 4 | 0.181 | 100 | 99.99 | 99.99 |
| | Embodiment 5 | 0.249 | 100 | 100 | 100 |
| | Embodiment 6 | 0.512 | 100 | 99.99 | 100 |
| | control sample | 0 | N/A | N/A | N/A |
| *Pseudomonas aeruginosa* | Embodiment 1 | 0.056 | — | 99.6 | 99.7 |
| | Embodiment 2 | 0.076 | 99.94 | 99.98 | 99.99 |
| | Embodiment 3 | 0.115 | 99.99 | 99.99 | 100 |
| | Embodiment 4 | 0.181 | 99.99 | 99.99 | 100 |
| | Embodiment 5 | 0.249 | 99.99 | 100 | 99.99 |
| | Embodiment 6 | 0.512 | 99.99 | 100 | 100 |
| | control sample | 0 | N/A | N/A | N/A |

Remark:
The control sample is an alginate dressing without the antimicrobial component.

2. A method for the detection of the content of polyhexamethylene guanide salt may be performed as the following.

Aqueous solution containing 1.5% (m/m) of agar is prepared, and when the agar solution is cooled to 50-55° C., 25.00±0.05 g of the solution is poured into a watch glass, to form an agar gel with a diameter of 90 mm and thickness of 3-4 mm to simulate the skin. PBS is added to an alginate fiber dressing with an area of 5×5 cm, to form an alginate gel, wherein the weight of PBS is 8 times of that of the alginate fiber dressing. The alginate gel may be hung up to drip dry for approximately 1 minute, when it has excessive free water. The alginate gel is spread on the surface of the agar gel, and is covered by a watch glass. The gel with the watch glass cover is sealed by a PE film for protection, and is placed in an incubator at a temperature of 37° C. for 72 hours and 168 hours. The agar gel is immersed by pure water, wherein the water is in twice amount of the agar gel, to establish an extraction system. The extraction system is sealed, and is placed in an incubator at a temperature of 37° C. for 24 hours, to obtain extraction solution. The extraction solution is filtered by a filter paper, the content of PHMB in the extraction solution is measured, and the amount of PHMB filtered out of the alginate dressing is calculated.

The measurement results are shown in the following table.

| Sample | Content of PHMB (%) | Filtration Rate in 72 hours (%) | Filtration Rate in 168 hours (%) |
|---|---|---|---|
| Embodiment 1 | 0.056 | 1.09 | 1.25 |
| Embodiment 2 | 0.076 | 1.01 | 1.15 |
| Embodiment 3 | 0.115 | 0.73 | 0.95 |
| Embodiment 4 | 0.181 | 0.58 | 0.76 |
| Embodiment 5 | 0.249 | 1.33 | 1.71 |
| Embodiment 6 | 0.512 | 0.42 | 0.55 |
| control sample | 0.409 | 9.23 | 11.81 |

Remark:
The control sample is a commercially available PHMB foam dressing approved by the US FDA.

3. A test of the content of PHMB in alginate fiber may be performed as the following:

(1) Principle: a color reaction occurs between guanidyl and eosin (a dye), and color change can be measured by the absorbance at the wavelength of 546 nm.

(2) Indicating solution: 500 ml of aqueous solution containing 0.2891 g/L of Eosin Y is prepared; and is filtered by a membrane filter having a pore size of 0.45 m, and the filtered solution is stored in dark.

(3) Buffer solution: 500 ml of aqueous solution of acetic acid and sodium acetate trihydrate in a mass ratio of 1:0.9514 is prepared where the molar concentration of [CH$_3$COO]$^-$ is 3.8532 mol/L; the aqueous solution is filtered by a membrane filter having a pore size of 0.45 m, and is sealed at room temperature for later use.

(4) Stabilizer solution: 2.000±0.0005 g of a blank alginate dressing, 10.5800±0.0005 g of trisodium citrate dihydrate, and 187.42±0.05 g of distilled water are provided; the trisodium citrate dihydrate is dissolved in 187.42 g of the distilled water in a 500 ml beaker; when the trisodium citrate dehydrate is completely dissolved, the blank alginate dressing is added into the solution; and the solution may be stirred by a stirring disperser to dissolve the blank alginate dressing at a low speed for 3 to 5 minutes; when the solution is stable, stirring speed of the stirring disperser is slowly increased, and finally the solution is stirred at the speed of 2200 r/min for 1.5 hours; lost distilled water is quantitatively replenished into the aqueous solution; the aqueous solution is filtered by a membrane filter having a pore size of 0.45 m, and the filtered aqueous solution is sealed at room temperature for later use.

Figure 3:
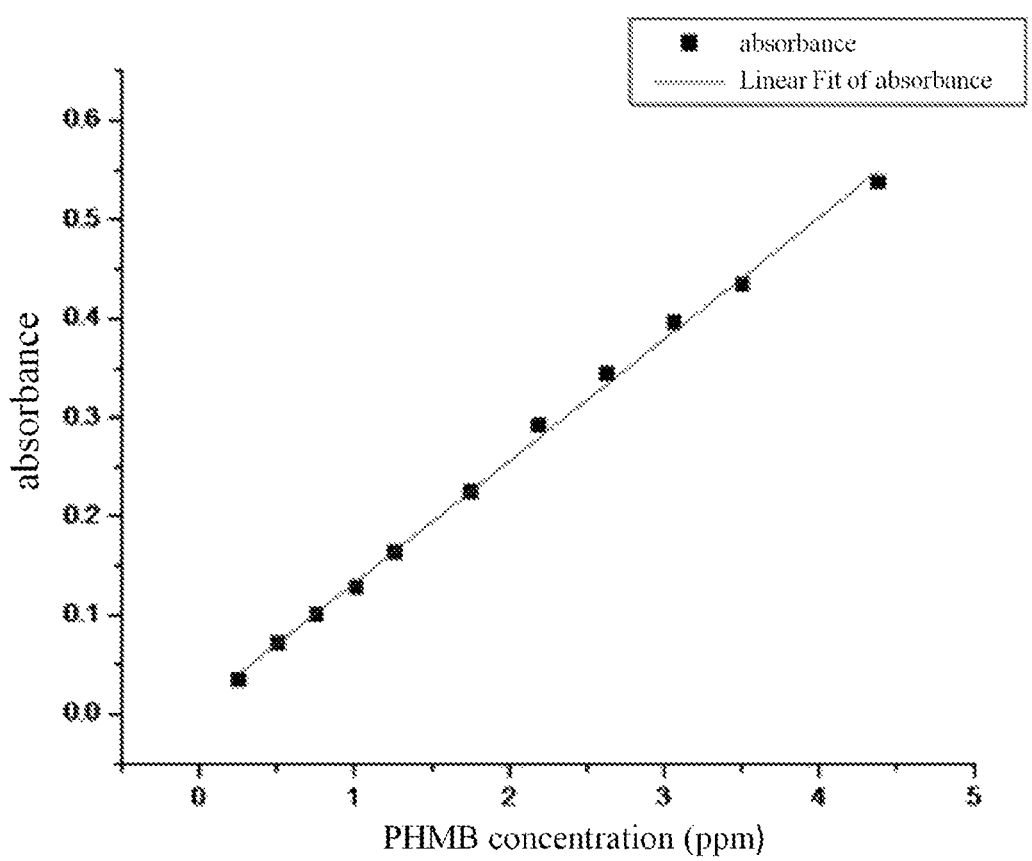
FIG. 3 is a standard curve to quantify polyhexamethylene biguanide.

(5) Standard curve drawing: guanidyl concentration and absorbance values are used to generate a standard curve, and a linear fitting curve equation is shown in FIG. 3.

The equation of the obtained standard curve is Y=0.12326*X+0.00942. The curve shows that polyhexamethylene biguanide hydrochloride (PHMB×HCl) at the concentration of 0.253 ppm to 4.380 ppm has a good linear relationship against the absorbance, and a correlation coefficient of the standard curve is 0.99763.

The content of PHMB in the alginate fiber dressings is calculated based on the above standard curve, the results are shown in the following table.

| Sample | Content of PHMB (%) |
|---|---|
| Embodiment 1 | 0.056 |
| Embodiment 2 | 0.076 |
| Embodiment 3 | 0.115 |
| Embodiment 4 | 0.181 |
| Embodiment 5 | 0.249 |
| Embodiment 6 | 0.512 |

To the skilled personnel in the art, the present disclosure should not be limited to the details of the above-described exemplary embodiments, and the present disclosure may be embodied in other specific forms without departing from the spirit or essential characteristics of the disclosure. Therefore, the present embodiments should be considered as illustrative and not restrictive, and the scope of the present disclosure is defined by the appended claims, but not by the above embodiments and descriptions, all changes in the meaning and scope of equivalent elements are included in the present disclosure. Any reference signs in the claims should not be treated as limitation of the claims.

In addition, it should be understood that although the description is described in terms of embodiments, not every embodiment includes only one independent technical solution. The description of the specification is merely for clarity, and the skilled personnel in the art should treat the specification as a whole, and the technical solutions in the respective embodiments may also be combined as appropriate to form other embodiments that can be understood by any skilled personnel in the art. It should be noted that the technical features not described in detail in the present disclosure may be implemented by any prior art.

Industrial application of the present disclosure is provided. The above-mentioned antimicrobial alginate fiber may be processed by combing, laying, and needle-punching, to form an alginate nonwoven. The alginate nonwoven may be processed by cutting, packaging, and sterilizing, to form an antimicrobial alginate fiber dressing product, such as an antimicrobial alginate towel, antimicrobial alginate nonwoven fabrics, and antimicrobial alginate gauze. The antimicrobial alginate fiber dressing product may be applied to acute and chronic wound care.

What is claimed is:

1. An antimicrobial alginate fiber, comprising a molecular structure as shown in formula (1):

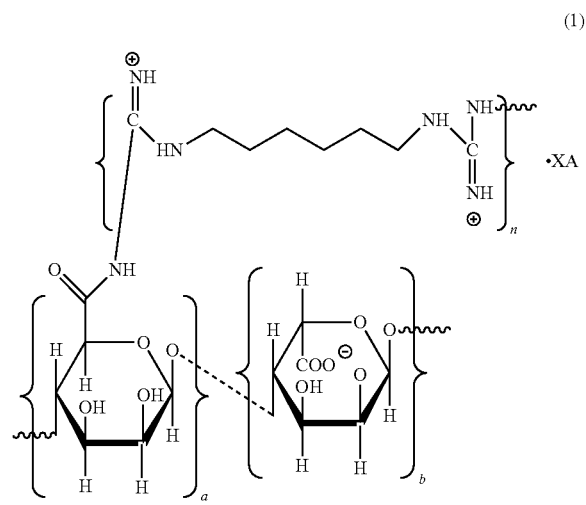

wherein, X is equal to 10 to 40, n is equal to 10 to 40, and A is anyone of hydrochloric acid, phosphoric acid, propionic acid, and gluconic acid.

2. The antimicrobial alginate fiber according to claim 1, wherein
a connection between a polyhexamethylene guanide salt and an alginate fiber is a covalent bond formed by interfacial reaction.

3. The antimicrobial alginate fiber according to claim 2, wherein
the alginate is selected from the group consisting of water soluble alginate salt, water insoluble alginate salt, and a blend of the water soluble alginate salt and the water insoluble alginate salt;
the water soluble alginate salt is anyone of sodium alginate, potassium alginate, magnesium alginate, and ammonium alginate;
the water insoluble alginate salt is anyone of calcium alginate and zinc alginate;
the blend of the water soluble alginate salt and the water insoluble alginate salt comprises blends formed of water soluble alginate salts with calcium ions or zinc ions as a crosslinking agent.

4. The antimicrobial alginate fiber according to claim 2, wherein
the polyhexamethylene guanide salt is selected from the group consisting of polyhexamethylene guanide hydrochloride, a derivative of the polyhexamethylene guanide hydrochloride, polyhexamethylene biguanide hydrochloride, a derivative of the polyhexamethylene biguanide hydrochloride, polyhexamethylene guanide phosphoric acid, a derivative of the polyhexamethylene guanide phosphoric acid, polyhexamethylene biguanide phosphoric acid, a derivative of the polyhexamethylene biguanide phosphoric acid, polyhexamethylene guanide propionic acid, a derivative of the polyhexamethylene guanide propionic acid, polyhexamethylene biguanide propionic acid, a derivative of the polyhexamethylene biguanide propionic acid, polyhexamethylene guanide gluconate, a derivative of the polyhexamethylene guanide gluconate, polyhexamethylene biguanide gluconate, and a derivative of the polyhexamethylene biguanide gluconate, and;

the polyhexamethylene guanide salt has a mass percentage in a range of 0.05% to 2.0%.

5. An application of an antimicrobial alginate fiber dressing, comprising:

processing the antimicrobial alginate fiber by combing, laying, and needle-punching, to form alginate nonwoven fabrics; or processing the antimicrobial alginate fiber by weaving, to form alginate gauze; and processing the alginate nonwoven fabrics or the alginate gauze by cutting, packaging, and sterilizing, to form the antimicrobial alginate fiber dressing, and the antimicrobial alginate fiber dressing is applied to acute and chronic wound care;

wherein the antimicrobial alginate fiber comprises a molecular structure as shown in formula (1):

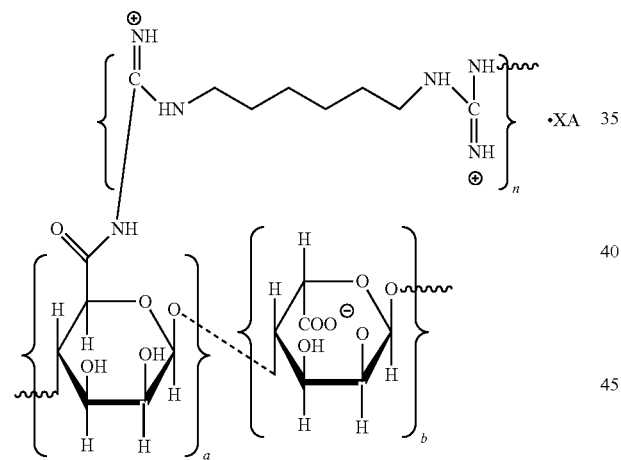

X is equal to 10 to 40, n is equal to 10 to 40, and A is anyone of hydrochloric acid, phosphoric acid, propionic acid, and gluconic acid.

6. The application according to claim 5, wherein the antimicrobial alginate fiber is obtained by loading polyhexamethylene guanide salt to an alginate fiber via a covalent bond formed by interfacial reaction.

7. The application according to claim 5, wherein the alginate is selected from the group consisting of water soluble alginate salt, water insoluble alginate salt, and a blend of the water soluble alginate salt and the water insoluble alginate salt;

the water soluble alginate salt is anyone of sodium alginate, potassium alginate, magnesium alginate, and ammonium alginate;

the water insoluble alginate salt is anyone of calcium alginate and zinc alginate;

the blend of the water soluble alginate salt and the water insoluble alginate salt comprises blends formed of water soluble alginate salts with calcium ions or zinc ions as a crosslinking agent.

8. The application according to claim 5, wherein the polyhexamethylene guanide salt is selected from the group consisting of polyhexamethylene guanide hydrochloride, a derivative of the polyhexamethylene guanide hydrochloride, polyhexamethylene biguanide hydrochloride, a derivative of the polyhexamethylene biguanide hydrochloride, polyhexamethylene guanide phosphoric acid, a derivative of the polyhexamethylene guanide phosphoric acid, polyhexamethylene biguanide phosphoric acid, a derivative of the polyhexamethylene biguanide phosphoric acid, polyhexamethylene guanide propionic acid, a derivative of the polyhexamethylene guanide propionic acid, polyhexamethylene biguanide propionic acid, a derivative of the polyhexamethylene biguanide propionic acid, polyhexamethylene guanide gluconate, a derivative of the polyhexamethylene guanide gluconate, polyhexamethylene biguanide gluconate, and a derivative of the polyhexamethylene biguanide gluconate, and;

the polyhexamethylene guanide salt has a mass percentage in a range of 0.05% to 2.0%.

* * * * *